United States Patent [19]

Gajdos et al.

[11] Patent Number: 5,114,928
[45] Date of Patent: May 19, 1992

[54] PHOSPHOLIPID-CONTAINING COMPOSITION, A PROCESS FOR ITS PREPARATION AND ITS USE AS AN EXCIPIENT FOR PHARMACEUTICAL SUBSTANCES

[75] Inventors: Benedikt Gajdos, Cologne; Heinz J. Mentzen, Neuss, both of Fed. Rep. of Germany

[73] Assignee: A. Nattermann & Cie. GmbH, Cologne, Fed. Rep. of Germany

[21] Appl. No.: 499,524

[22] PCT Filed: Aug. 1, 1989

[86] PCT No.: PCT/EP89/00898

§ 371 Date: Jun. 19, 1990

§ 102(e) Date: Jun. 19, 1990

[87] PCT Pub. No.: WO90/01269

PCT Pub. Date: Feb. 22, 1990

[30] Foreign Application Priority Data

Aug. 9, 1988 [DE] Fed. Rep. of Germany ....... 3826946

[51] Int. Cl.$^5$ .............................. A61K 9/20; A23J 7/00
[52] U.S. Cl. ....................................... 514/25; 424/450; 514/78; 514/777; 514/970; 514/974
[58] Field of Search .................. 424/450; 514/25, 78, 514/777, 974, 970

[56] References Cited

U.S. PATENT DOCUMENTS 3,012,888 12/1961 Davis ................................. 424/450

FOREIGN PATENT DOCUMENTS

EP72469 2/1983 European Pat. Off. .

OTHER PUBLICATIONS

Chemical Abstracts, vol. 109, No. 19, Abstract 169028v, Nov. 7, 1988.
Chemical Abstracts, vol. 104, No. 10, Abstract 74837r, Mar. 10, 1986.

*Primary Examiner*—Ronald W. Griffin
*Attorney, Agent, or Firm*—Burns, Doane, Swecker & Mathis

[57] ABSTRACT

The invention relates to a solid phospholipid composition with a high phosphatidylcholine content which, in addition to the corresponding phospholipids, contains Palatinit and if appropriate one or more other auxiliaries, and a process for its preparation and its use as an oral presentation form.

7 Claims, No Drawings

PHOSPHOLIPID-CONTAINING COMPOSITION, A PROCESS FOR ITS PREPARATION AND ITS USE AS AN EXCIPIENT FOR PHARMACEUTICAL SUBSTANCES

DESCRIPTION

The invention relates to new phospholipid-containing compositions which, in addition to the corresponding phospholipids, contain Palatinit as a solidifying agent and if appropriate one or more auxiliaries, and a process for their preparation. The composition can be used as a solid oral presentation form.

Phospholipids occur widely in nature and can be obtained from animal and vegetable materials. The main sources are eggs (egg lecithin) and soya (soya lecithin), oil seeds and oil fruits, such as, for example, coconutcopra, palm kernels, groundnuts, rape, sunflower kernels, oil palms and olives. The phospholipids are predominantly obtained as a by-product in the production of vegetable oils. During this, a viscous mass is obtained by the so-called desliming of the vegetable oils, which is effected by passing small amounts of steam or water into the crude oil at elevated temperatures. This so-called lecithin slime has a varying composition, depending on its origin:
14–36% by weight of vegetable oil
27–57% by weight of water and
59–8% by weight of phospholipids.

The commercially available crude lecithin is obtained by drying the lecithin slime in an evaporator at elevated temperatures (80° C.) over a relatively long period of time (from 6–12 hours) or at 100° C. in a thin film evaporator with a shorter residence time.

The most important crude lecithin is soya lecithin, which, after drying, contains about 52% by weight of phospholipids, 35% by weight of oils and fatty acids, 10% by weight of glycolipids and sugars, 2% by weight of non-hydrolysable portions and 1% by weight of water.

The so-called de-oiled phospholipids (or de-oiled crude lecithin which contains only small amounts of oil and other concomitant lipids) are obtained by treatment with corresponding solvents, for example acetone. The lecithin fractions obtained have varying phospholipid compositions depending on their origin:

Soya Lecithin
about
30% of phosphatidylcholine,
1–2% of lysophosphatidylcholine,
22% of phosphatidylethanolamine,
1–2% of lysophosphatidylethanolamine,
3–4% of phosphatidylserine,
18% of phosphatidylinositol,
13% of phytoglycolipids,
2% of phosphatidic acid and
8% of concomitant lipids.

Egg Lecithin
73% of phosphatidylcholine,
5–6% of lysophophatidylcholine,
15% of phosphatidylethanolamine,
2–3% of lysphosphatidylethanolamine,
1% of phosphatidylinositol,
2–3% of sphingomyelin and
1% of plasmologues.

Rape Lecithin
30–32% of phosphatidylcholine,
3% of lysophosphatidylcholine,
30–32% of phosphatidylethanolamine,
3% of lysophosphatidylethanolamine,
14–18% of phosphatidylinositol,
1% of lysophosphatidylinositol,
10% of phytoglycolipids,
1% of phosphatidic acid and
2–3% of concomitant lipids.

Saflower Lecithin
32–39% of phosphatidylcholine,
1–2% of lysophosphatidylcholine,
14–17% of phosphatidylethanolamine,
2% of lysophosphatidylethanolamine,
21–27% of phosphatidylinositol,
1% of lysophosphatidylinositol,
15–28% of concomitant lipids.

The individual lecithins can also be purified by known processes and the corresponding phospholipids can be separated into the individual constituents, such as phosphatidylcholine, phosphatidylethanolamine, phosphatidylinositol, phosphatidylserine, phosphatidylglycerol, lysophosphatidylcholine, lysophosphatidylethanolamine, lysophosphatidylserine or lysophosphatidylglycerol, or olefinic mixtures can be prepared.

The phospholipid mixtures of very different composition, starting from wet lecithin slime, crude lecithin and de-oiled lecithin up to phospholipid mixtures of defined composition or even pure phospholipids, such as, for example, phosphatidylcholine, have physical properties which deviate very widely from one another. The phospholipid mixtures have a very different consistency from liquid to viscous-plastic. The plasticity of the lecithin increases with its degree of purity, that is to say as the phosphatidylcholine content increases and the oil content decreases.

Since lecithin and, to an increasing degree, highly pure lecithin are available, as is known, as a very highly viscous, paste-like composition, working already presents considerable difficulties because of the viscosity of the lecithin. The lecithin is difficult to meter, and because of its viscous consistency remains stuck to the equipment with which it comes into contact, so that the residues which remain require frequent and expensive cleaning of the equipment.

It is therefore often necessary to make do with preparing viscous or pasty preparations for the corresponding use from the crude lecithin by addition of auxiliaries.

If pure lecithin or particularly highly pure lecithin is used, the problem that the increasing purity of the lecithin results in the lecithin becoming increasingly sparingly soluble arises in particular.

The hygroscopic nature of the highly pure lecithin which renders mixing or coating of the highly pure lecithin with fat-like waxy substances practically impossible is a further hindrance.

Attempts have therefore often been made to convert lecithin into forms which allow easier processing.

Thus, U.S. Pat. No. 2,057,695 describes a process for the preparation of powdered oil-free phosphatide products which have a very high lecithin content in the end product. In this process, crude phosphatide is de-oiled by extraction several times with acetone, water is added to the oil-free product, the residue of undissolved material is removed and the aqueous phosphatide emulsion which remains is further dried by spray drying or roller drying. Additions of sugar may be made here. The oil-free aqueous lecithin solution, which has a very high water content (about 20 to 50 times the amount), is then mixed directly with a stabilizer, such as, for example, salicylic acid, and can then subsequently be dried. If sugar is added, for example sucrose, a phospholipid content of a maximum of 60% can be achieved.

U.S. Pat. No. 3,012,888 describes oil-free phosphatide products which contain 1–5% of monosaccharide and are obtained by adding a 40% strength solution of corresponding monosaccharide to crude lecithin, heating the mixture to 60°–70° C. until a homogeneous mass is obtained, subsequently drying the mass in vacuo and removing the oil with acetone. Finally, the residue solution is removed in vacuo. The aim of the application is the preparation of storage-stable phosphatide products starting from aqueous solution systems. If non-reducing sugars are used, no satisfactory results are obtained.

DE-PS 642,932 describes an industrial process for drying lecithin and subsequent coating with wax-like substances, whereas in DE-PS 973,741, drying by comminution under the influence of heat takes place, after de-oiling with acetone.

DE-PS 508,353 (U.S. Pat. No. 1,776,721) contains technical instructions for mixing lecithin with flour or flour products.

U.S. Pat. No. 1,988,050 describes a mixture of phospholipids crude (lecithin) and cereal germ which is de-oiled or dried with alcohol. In U.S. Pat. No. 2,632,705, in addition to cereal flour, fatty acid esters are added to the lecithin.

In U.S. Pat. No. 2,430,553, aqueous sugar solution is added to crude lecithin and the mixture is de-oiled and dried in a two-bath process. Products which have only a low lecithin content are obtained.

U.S. Pat. No. 2,447,726 describes mixing of lecithin with gelose, a reducing sugar obtained form "Irish moss", and U.S. Pat. No. 2,708,631 describes a solution of a maximum of 20% of lecithin in dextrose.

U.S. Pat. No. 2,973,381 describes a composition of phospholipid and tocopherol (vitamin E) whereas in U.S. Pat. No. 3,480,544 phospholipids and $SiO_2$ are mixed with one another.

In U.S. Pat. No. 2,929,723, liquid aromatics are converted into solid products with the aid of lecithin (0.1–5%).

All the previous processes have the disadvantage that either only small lecithin contents are present in the product or expensive product preparation is necessary. In addition, the consistency of the product is often unsatisfactory.

The aim of the present invention is therefore to discover an additive and a method with which phospholipid mixtures from different starting substances are converted into products which can also have a high phosphatidylcholine content and the consistency of which can be controlled by the choice of additive and its amount.

This object is achieved by a phospholipid-containing composition which contains sugar as a solidifying agent and customary auxiliaries, characterized in that a 1:1 mixture of glucopyranosido-1,6-mannitol and glucopyranosido-1,6-sorbitol (PALATINIT) in a weight ratio of phospholipid:PALATINIT of 1:20 to 20:1 is present as the sugar.

Surprisingly, it has now been found that it is possible to mix PALATINIT, a non-reducing sugar, with highly pure lecithin and in this way to obtain products which have an extremely solid consistency and are not sticky.

It is also completely surprising that PALATINIT and lecithin can be mixed with one another directly, without the customary antiadhesives, and the sticky properties of the lecithin and its strong hygroscopic character, which is otherwise a great hindrance to effective processing, can be neutralized completely by means of the PALATINIT, so that solid stable products which are very easy to handle are formed in a one-stage process. The consistency of the product can be controlled here from pasty to very solid via the ratio of PALATINIT to phospholipid. The weight ratio of phospholipids:PALATINIT is 1:20 to 20:1, preferably 4:1 to 20:1.

PALATINIT is a non-reducing sugar and the tradename for a hydrogenated isomaltulose which consists of a 1:1 mixture of glucopyranosido-1,6-mannitol and glucopyranosido-1,6-sorbitol and has a purity of >99% (J. S. Hoeven, Caries Res., 13 (1979), page 301).

The composition can contain naturally occurring or synthetic phospholipids.

All products in which the phospholipid content can vary from 5 to 98%, such as, for example, egg lecithin (about 80% of phosphatidylcholine, the remainder being other phospholipids), soya lecithin (about 77% of phospholipids, 13% of phytoglycolipids, 2% of phosphatidyl acid and 8% of concomitant lipids) or highly pure phospholipids having a phosphatidylcholine content of up to 96%, can be employed as the phospholipid-containing starting mixtures. Phospholipid mixtures of different composition can likewise also be employed. The phospholipid fractions can be obtained from soya beans, rape, sunflower kernels and other oil fruits and oil seeds, but preferably from soya beans, by processes which are known per se in accordance with DE-OS 30 47 048, DE-OS 30 47 012 and DE-OS 30 47 011.

Auxiliaries which can be employed, for example for improving the taste, are the customary aroma substances, such as, for example, vanillin, aniseed, caramel, chocolate, malt, peppermint oil or fruit aromas, such as, for example, banana, orange, raspberry or mixtures thereof.

Sweeteners, for example sodium cyclamate, saccharin, xylitol, cane sugar (sucrose), glucose, fructose or maltose or other sweetener derivatives, can likewise also be used. It is also possible to combine several of the abovementioned auxiliaries, in order thus to be able to prepare the composition of desired taste. The amount of auxiliaries in the composition can be up to 5% by weight, based on the total weight. The products can be processed by customary methods into grains, granules, bars, chewable tablets and the like, or converted into other forms which allow further processing without problems.

The mixture of lecithin or phospholipid/PALATINIT can be prepared by producing a lecithin solution, mixing this with the corresponding amount of PALATINIT or PALATINIT solution and subsequently freeing the mixture from adhering solvent in a roll mill drier or spray drier.

Surprisingly, however, it is also possible to prepare the composition by adding a melt of PALATINIT to lecithin or phospholipids under the influence of heat and mixing the components by customary methods until a homogeneous mass has formed. The customary aroma substances, such as, for example, vanillin, aniseed, caramel, chocolate, malt, peppermint oil or fruit aromas, such as, for example, banana, orange, raspberry or mixtures thereof, can then be added to this homogeneous phase.

It is also possible to add sweeteners, for example sodium cyclamate, saccharin, xylitol, cane sugar (sucrose), glucose, fructose or other sweetener derivatives or corresponding combinations.

After its homogenization, the entire mass can be shaped under plastic conditions under the influence of heat or, after cooling, processed to grains, granules, bars, tablets and the like, or converted into other forms which allow further processing without problems.

The composition is plastic at temperatures from 50° C. to 80° C., so that it is preferable to prepare the composition at these temperatures by mixing the constituents, and also to convert it into oral presentation forms. The composition is preferably used as an oral presentation form. It can in this way also serve as an excipient for medicaments for oral administration, that is to say pharmaceutically active substances.

Oral presentation forms are, for example, granules, tablets, chewable tablets, bars/toffees, film-coated tablets and filled hard gelatin capsules.

The invention is described in more detail by the following examples:

EXAMPLE 1

| | |
|---|---|
| Purified soya lecithin (about 76% of phosphatidylcholine) | 3947 g |
| Palatinit | 2008 g |
| Vanillin | 45 g |

The purified soya lecithin is kneaded at 80° C. in the customary manner and the hot PALATINIT mass at 140° C. is added. When the mixture has reached a temperature of 80° C. vanillin is added and the mixture is kneaded until a homogeneous mass has formed. The product can be shaped under plastic conditions under the influence of heat or, after cooling, processed to grains, granules, bars, chewable tablets and the like, it also being possible to incorporate pharmaceutically active substances, if appropriate, so that the composition is used as an excipient.

EXAMPLE 2

| | |
|---|---|
| Purified soya lecithin (about 76% of phosphatidylcholine) | 6579 g |
| PALATINIT | 3346 g |
| Vanillin | 75 g |

Preparation analagous to Example 1.
A solid product is formed.

EXAMPLE 3

| | |
|---|---|
| Purified soya lecithin (about 76% of phosphatidylcholine) | 2831 g |
| PALATINIT | 1145 g |
| Vanillin | 24 g |

Preparation analagous to Example 1.
A solid product is formed.

EXAMPLE 4

| | |
|---|---|
| Purified soya lecithin (about 76% of phosphatidylcholine) | 3875 g |
| PALATINIT | 1078 g |
| Vanillin | 47 g |

Preparation analagous to Example 1.
A solid product is formed.

EXAMPLE 5

| | |
|---|---|
| Purified soya lecithin (about 76% of phosphatidylcholine) | 118.5 g |
| PALATINIT | 10.0 g |
| Vanillin | 1.5 g |

Preparation analagous to Example 1.
A mass which has very viscous, pasty properties but is not sticky is formed.

EXAMPLE 6

| | |
|---|---|
| Highly pure phospholipids (about 98% of phosphatidylcholine) | 75.27 g |
| PALATINIT | 23.98 g |
| Vanillin | 0.75 g |

Preparation analagous to Example 1.
A solid product is formed.

EXAMPLE 7

| | |
|---|---|
| Highly pure phospholipids (about 98% of phosphatidylcholine) | 57.57 g |
| PALATINIT | 41.73 g |
| Vanillin | 0.70 g |

Preparation analagous to Example 1.
A solid product is formed.

EXAMPLE 8

| | |
|---|---|
| Highly pure phospholipids (about 98% of phosphatidylcholine) | 81.41 g |
| PALATINIT | 18.11 g |
| Vanillin | 0.48 g |

Preparation analagous to Example 1.
A solid product is formed.

EXAMPLE 9

| | |
|---|---|
| Highly pure phospholipids (about 98% of phosphatidylcholine) | 90.25 g |
| PALATINIT | 9.01 g |
| Vanillin | 0.74 g |

Preparation analagous to Example 1.
A product which has a very viscous, pasty consistency but is not sticky is formed.

EXAMPLE 10

| | |
|---|---|
| Highly pure phospholipids (about 98% of phosphatidylcholine) | 92.43 g |
| PALATINIT | 7.02 g |

-continued

| | |
|---|---|
| Vanillin | 0.45 g |

Preparation analagous to Example 1.
The product has the same properties as in Example 9.

EXAMPLES 11 TO 15

These correspond to Examples 1 to 5, but the vanillin is replaced by the same amount of xylitol and vanillin in the ratio 1:1. Products with the same properties as in Examples 1 to 5 are obtained.

EXAMPLES 16 TO 20

These correspond to Examples 6 to 10. The vanillin is replaced by the same amount of aniseed. Products with the properties of Examples 6 to 10 are formed.

EXAMPLE 21

| | |
|---|---|
| Phospholipid-PALATINIT product (for example from Example 2 or 12) | 1440 g |
| Powdered PALATINIT | 315 g |
| Silicon dioxide | 45 g |

The finished solid product from Example 2 is ground to free-flowing granules by customary processes and the granules are then mixed with the PALATINIT powder and the SiO$_2$. Chewable tablets having a diameter of 16 mm (weight 1.5 g) and those having a diameter of 22 mm (weight 2.5 g) are pressed in a customary tablet press.

EXAMPLE 22

| | |
|---|---|
| Phospholipid-PALATINIT product (for example from Example 2 or 12) | 800 g |
| Powdered PALATINIT | 160 g |
| Silicon dioxide | 25 g |
| Caramel aroma | 15 g |

Preparation of chewable tablets analogous to Example 21.

EXAMPLE 23

| | |
|---|---|
| Phospholipid-PALATINIT product (for example from Example 2 or 12) | 527 g |
| Powdered PALATINIT | 160 g |
| Silicon dioxide | 25 g |
| Finely powdered glyceride mixture | 15 g |

Preparation of chewable tablets analogous to Example 21.

EXAMPLE 24

| | |
|---|---|
| Phospholipid-PALATINIT product (for example from Example 2 or 12) | 777 g |
| Powdered fructose | 117 g |
| Silicon dioxide | 25 g |
| Powdered cacao | 75 g |
| Vanillin | 6 g |

Preparation of chewable tablets analogous to Example 21.

EXAMPLE 25

| | |
|---|---|
| Phospholipid-PALATINIT product (for example from Example 2 or 12) | 777 g |
| Powdered PALATINIT | 72 g |
| Powdered fructose | 10 g |
| Silicon dioxide | 25 g |
| Cream aroma | 20 g |
| Vanillin | 6 g |

Preparation of chewable tablets analogous to Example 21.

For Examples 26–29, a soya lecithin of the following composition was used: 35% of phosphatidylcholine, 26–33% of other phospholipids and other concomitant substances and 32–39% of oil.

EXAMPLE 26

| | |
|---|---|
| Lecithin (35% of phosphatidylcholine) | 715 g |
| PALATINIT | 1760 g |
| Vanillin | 25 g |

EXAMPLE 27

| | |
|---|---|
| Lecithin (35% of phosphatidylcholine) | 1072 g |
| PALATINIT | 1403 g |
| Vanillin | 25 g |

EXAMPLE 28

| | |
|---|---|
| Lecithin (35% of phosphatidylcholine) | 3500 g |
| PALATINIT | 2440 g |
| Vanillin | 60 g |

EXAMPLE 29

| | |
|---|---|
| Lecithin (35% of phosphatidylcholine) | 3330 g |
| PALATINIT | 630 g |
| Vanillin | 40 g |

The products of Examples 26–29 are solid.
For Examples 30 to 33, in each case one of the compositions shown below is used.

| | |
|---|---|
| Composition I | |
| Highly purified phospholipids (up to 98% of phosphatidylcholine) | 1400 g |
| PALATINIT | 600 g |
| Composition II | |
| Purified soya lecithin (about 76% of phosphatidylcholine) | 400 g |
| PALATINIT | 600 g |
| Composition III | |
| Lecithin (35% of phosphatidylcholine) | 1400 g |
| PALATINIT | 600 g |

EXAMPLE 30

Lecithin-multivitamin Chewable Tablets

| | |
|---|---|
| 1. Base (I, II or III) | 1944.00 mg |
| 2. Vitamin A, 500,000 IU/g | 4.00 mg |

-continued

| | |
|---|---|
| (retinolacetate) | |
| 3. Vitamin B$_1$ (thiamine chloride.HCl) | 0.25 mg |
| 4. Vitamin B$_2$ (riboflavin) | 1.00 mg |
| 5. Vitamin B6 (pyridoxine.HCl) | 1.00 mg |
| 6. Vitamin B12 (cyanocobalamine) | 1.00 μg |
| 7. Vitamin C | 50.00 mg |
| 8. Vitamin D, 100,000 IU/g (colecalciferol) | 2.00 mg |
| 9. Vitamin E (50%) (tocopherol acetate) | 1.00 mg |
| 10. Nicotinamide | 10.00 mg |
| 11. Folic acid | 0.25 mg |
| 12. PALATINIT PF | 556.00 mg |
| 13. Vanillin DAB 8 | 17.00 mg |
| 14. Kollidon 25 | 143.00 mg |
| 15. Syloid 244 | 29.00 mg |
| 16. Sodium chloride | 0.60 mg |
| 17. Aerosil R 972 | 29.00 mg |
| 18. Aspartame | 0.60 mg |
| 19. Stearic acid | 57.00 mg |
| 20. Apricot aroma | 14.50 mg |

The substances are mixed together and pressed to biplanar chewable tablets having a diameter of 25 mm and a weight of 2.86 g with the aid of a tablet press.

EXAMPLE 31

Lecithin-multivitamin-mineral Chewable Tablets

The following substances are also added to the mixture from Example 1:

| | |
|---|---|
| 1. Copper (II) sulphate | 0.50 mg |
| 2. Manganese (II) sulphate | 0.20 mg |
| 3. Iron (II) sulphate | 20.00 mg |
| 4. Cobalt (II) sulphate | 0.40 mg |
| 5. Magnesium carbonate | 20.00 mg |
| 6. Zinc oxide | 0.05 mg |
| 7. Calcium hydrogen phosphate | 98.85 mg |

This entire mixture is then pressed to biplanar chewable tablets having a diameter of 25 mm and a weight of 3.0 g with the aid of a tablet press.

EXAMPLE 32

Lecithin-containing Antacid Chewable Tablets

| | |
|---|---|
| 1. Base (I, II or III) | 1000.00 mg |
| 2. Alugel (dried aluminum hydroxide gel, Giulini-Chemie, Ludwigshafen) | 505.00 mg |
| 3. PALATINIT PF | 407.00 mg |
| 4. Skimmed milk powder | 500.00 mg |
| 5. Sodium cyclamate | 3.00 mg |
| 6. Kollidon 25 | 50.00 mg |
| 7. Syloid 244 | 20.00 mg |
| 8. Peppermint essence | 5.00 mg |
| 9. Magnesium stearate | 10.00 mg |

The base is mixed with the Alugel granules and other substances and the mixture is then pressed to chewable tablets weighing 2.5 g.

EXAMPLE 33

| | |
|---|---|
| 1. Base (I, II or III) | 1000.00 mg |
| 2. Wheat bran | 1000.00 mg |
| 3. PALATINIT PF | 500.00 mg |

-continued

| | |
|---|---|
| 4. Syloid 244 | 35.00 mg |
| 5. Kollidon 25 | 150.00 mg |
| 6. Aerosil R 972 | 25.00 mg |
| 7. Aspartame | 0.70 mg |
| 8. Vanillin DAB 8 | 20.00 mg |
| 9. Stearic acid | 60.00 mg |

Bars of various sizes are produced with this mixture.

In order to demonstrate the superiority of PALATINIT as a solidifying agent over known sugars, comparison experiments are carried out.

Tabletting experiments were carried out with granules which contained lecithin carbohydrate and have been obtained by mixing the solid starting substances. The granules were obtained by means of a AMK kneader or Berstorff extruder. After mixing the granules with the auxiliaries listed, the tablets were pressed in a biplanar stamp form of 25 mm diameter in a tablet press of the type Hillian RT 116.

The following amounts of substances were used for all the experiments:

| | |
|---|---|
| Purified soya lecithin: (phosphatidylcholine content of about 76%) | 55.65 g |
| Carbohydrate: | 23.85 g |
| Tabletting auxiliaries | |
| Avicel PH: | 20 g |
| Aerosil 200: | 0.50 g |
| Stearic acid (optional): | 3 g |

(if stearic acid is used, only 17 g of Avicel PH are employed).

The results can be found in Table 1 (without addition of stearic acid) and in Table 2 (with addition of stearic acid):

TABLE 1

| | Carbohydrate | | | | |
|---|---|---|---|---|---|
| | Glucose | Fructose | Xylitol | Mannitol | Palatinit |
| Effect sticking to tablet stamps | yes | yes | yes | yes | no |
| "Capping" of the tablets | yes | yes | yes | no | no |
| Pressing possible | no | no | no | no | yes |

"Capping" of the tablets means that these disintegrate into two flat (cap) halves on leaving the pressing die. A yes in this column leads to a devaluation of the properties.

TABLE 2

(with addition of stearic acid)

| | Carbohydrate | | | | |
|---|---|---|---|---|---|
| | Glucose | Fructose | Xylitol | Mannitol | Palatinit |
| Effect sticking to tablet stamps | yes | yes | yes | yes | no |
| "Capping" of the tablets | no | no | yes | no | no |
| Pressing possible | no | no | no | no | yes |

The superiority of the product according to the invention of lecithin plus PALATINIT can be clearly seen from the results, since this mixture is the only one which leads to non-sticking forms which can be pressed.

We claim:

1. A phospholipid-containing composition comprising phospholipid and sugar in a weight ratio of 1:20 to 20:1, said sugar comprising a 1:1 mixture of glucopyranosido-1,6-mannitol and glucopyranosido-1,6-sorbitol.

2. The phospholipid-containing composition as claimed in claim 1, wherein said phospholipid comprises naturally occurring or synthetic phospholipids.

3. The phospholipid-containing composition as claimed in claim 2, wherein said naturally occurring phospholipid comprises soya lecithin or a highly purified fraction thereof.

4. A pharmaceutical composition for oral administration comprising a pharmaceutically active substance and the phospholipid-containing composition as claimed in claim 1.

5. A method for administering a pharmaceutically active substance, said method comprising administering an orally active pharmaceutical substance and a phospholipid-containing composition of claim 1 to a patient in need of treatment.

6. A process for the preparation of a phospholipid-containing composition, said process comprising heating sugar, said sugar comprising a 1:1 mixture of a glucopyranosido-1,6-mannitol and glucopyranosido-1,6-sorbitol to obtain a melt; and adding phospholipid to said sugar with mixing until the mixture of sugar and phospholipid is homogeneous, wherein the weight ratio of phospholipid sugar is in the range of 1:20 to 20:1.

7. A process for the preparation of a phospholipid-containing composition, said process comprising heating sugar, said sugar comprising a 1:1 mixture of glucopyranosido-1,6-mannitol and glucopyranosido-1,6-sorbitol to obtain a melt; and adding said sugar to phospholipids under the influence of heat to obtain a phospholipid-containing composition, wherein the weight ratio of phospholipid sugar is in the range of 1:20 to 20:1.

* * * * *